United States Patent [19]

Pascone

[11] Patent Number: 4,791,218

[45] Date of Patent: Dec. 13, 1988

[54] CRYSTALLINE AMINO-PROTECTED AMINO ACIDS AND METHOD OF PREPARATION

[75] Inventor: John M. Pascone, Neshanic Station, N.J.

[73] Assignee: Ortho Pharmaceutical Corporation, Raritan, N.J.

[21] Appl. No.: 866,546

[22] Filed: May 23, 1986

[51] Int. Cl.⁴ .......................................... C07C 125/073
[52] U.S. Cl. ..................................................... 560/158
[58] Field of Search ........................................ 560/158

[56] References Cited

PUBLICATIONS

Ault, "Techniques and Experiments for Organic Chemistry," 4th ed., pp. 44–59 (1983).
Irving, J. Org. Chem., 24, pp. 1979–1983, (1959).
Greenstein, J. Org. Chem., 2, pp. 480–483, (1937).
Greenstein, J. Biol. Chem. 182 pp. 451–456, (1950).

*Primary Examiner*—Michael L. Shippen

[57] ABSTRACT

Crystalline alpha-epsilon amino-protected L-lysine derivatives are disclosed as well as a crystallization method therefor. These crystalline compounds are obtained in relatively high yields.

18 Claims, 2 Drawing Sheets

CRYSTALLINE AMINO-PROTECTED AMINO ACIDS AND METHOD OF PREPARATION

DESCRIPTION

1. Technical Field

This invention relates to amino-protected amino acids in crystalline form, and, in particular, to a method for obtaining such acids in high yields. More particularly, this invention relates to crystalline amino-protected L-lysine, having both its alpha-amino group and its epsilon-amino group protected, and to a method of preparing it in a relatively high yield.

2. Background Art

Amino-protected amino acids, i.e., amino acids having one or more of their amino functional groups protected or blocked by an amino-protective group, and sometimes called N-blocked amino acids, are widely used in the field of biochemistry. Commercially, amino-protected amino acids are useful as starting or intermediate compounds in the chemical synthesis of peptides, polypeptides and proteins, particularly new polypeptides that are biologically important.

One common difficulty of peptide synthesis, particularly of long chain polypeptide synthesis, is obtaining such polypeptides in relatively high yields. It is well known that unless each of the reactions in a multi-step peptide synthesis can be made nearly quantitative, the yield of product that can be prepared from reasonable amounts of starting materials will be exceedingly small. Thus, it is desirable that an amino-protected amino acid used as the starting compound in the chemical synthesis of biologically active polypeptides be in a purified crystalline form, so that a reasonable amount of starting material can be used.

L-lysine derivatives are particularly useful in the chemical synthesis of thymic hormone described and claimed in U.S. Pat. No. 4,190,646 to Goldstein et al. A particularly preferred L-lysine derivative, commonly used, is alpha-tert-butyloxycarbonyl-epsilonbenzyloxycarbonyl-L-lysine.

Most amino acid derivatives containing a tert-butyloxycarbonyl moiety as the amino-protective group can be crystallized from extractive solvent mixtures of ethyl acetate-hexane. However, alphatertiary-butyloxycarbonyl-epsilon-benzyloxycarbonylL-lysine has not been heretofore available in crystalline form. Consequently, these derivatives are frequently crystallized and supplied as dicyclohexylamine salts. The use of these salts introduces an extra recovery step before the tert-butyloxycarbonyl protected amino acid can be used in a desired synthesis procedure, and are, therefore, neither desirable nor recommended.

Alpha-tert-butyloxycarbonyl-epsilonbenzyloxycarbonyl-L-lysine is available commercially as a yellowish oil. For example, it is available from Chemical Dynamics Corporation, South Plainfield, N.J., and a listing for it can be found in its 1984-85 catalog. According to that supplier, its purity is greater than 99 percent as determined by thin layer chromatography. Other listings of this aminoprotected amino acid can also be found in the 1984/85 catalog of Bachem, Inc., Torrance, Calif., and in the 1984 catalog of Sigma Chemical Co., St. Louis, Mo. None of these materials are crystalline, however, and contain undesirable impurities.

There is a need, therefore, for a relatively high-purity amino-protected L-lysine derivative in crystalline form, particularly for an L-lysine derivative having both its alpha-amino group and its epsilon-amino group protected, and for a method for preparing such compounds. It would also be desirable to have relatively high-purity crystalline alpha-tert-butyloxycarbonyl-epsilon-benzyloxycarbonyl-L-lysine for use in polypeptide synthesis.

BRIEF DESCRIPTION OF THE DRAWINGS

In the drawings forming a portion of the disclosure of this invention.

SUMMARY OF THE INVENTION

Figure 1:
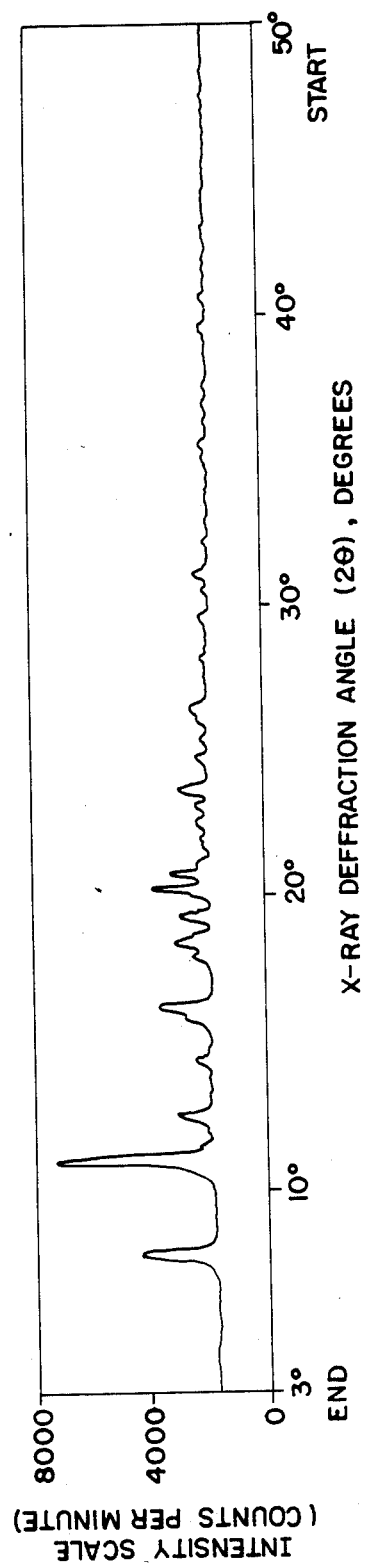
FIG. 1 sets forth the X-ray diffraction pattern in line profile for crystalline alpha-tert-butyloxycarbonyl-epsilon-benzyloxycarbonyl-L-lysine of Example 1 herein and prepared by a method of this invention.

This invention provides amino-protected amino acids in crystalline form, and, in one aspect, to a method for obtaining a relatively high-purity amino-protected L-lysine in relatively high yields. Specifically, crystalline alpha-tertbutyloxycarbonyl-epsilon-benzyloxycarbonyl-L-lysine, having a melting point of about 71° C. to about 78° C., can be prepared when practicing this invention. This material has a purity of at least about 99.5 percent.

According to a method aspect of this invention, crystalline alpha-epsilon amino-protected L-lysine is extractively isolated from a mother liquor constituted by a substantially water-immiscible polar solvent for the amino-protected L-lysine and a phase modifier. The water content of the mother liquor is maintained at no more than about 0.9 weight percent. The solubility of the alpha-epsilon amino-protected L-lysine in the solution is reduced, in the presence of a nucleating agent, until the mother liquor becomes supersaturated with respect to the alpha-epsilon amino-protected L-lysine and the latter separates out as a solid crystalline phase which is then harvested.

The solubility of the L-lysine derivative in the polar solvent can be reduced by the addition of a liquid nonpolar phase modifier alone or in combination with a reduction in temperature to below ambient temperature. Crystallization can be initiated with a nucleating seed crystal of the same alpha-epsilon amino-protected L-lysine or by an inert nucleation promoter.

In a preferred embodiment, the method of the present invention provides a high yield, usually in excess of above 90 percent of the theoretically calculated amount, of crystalline alpha-tert-butyloxycarbonyl-epsilon-benzyloxycarbonyl-L-lysine having a purity of above 99.5 percent, calculated as the free acid form of the L-isomer.

This crystalline L-lysine derivative is useful for the production of chemically synthesized polypeptide derivatives as described, for example, in U.S. Pat. Nos. 4,190,646 and 4,215,112 to Goldstein, et al.; 4,232,008 to Goldstein; 4,289,759 to Heavner, et al.; 4,298,523 and 4,250,086, both to Heavner, the pertinent disclosures of which are incorporated herein by reference.

For example, the crystalline alpha-epsilon amino-protected L-lysine derivatives prepared by the method of this invention are useful for the "solid phase" peptide synthesis involved in the stepwise addition of N- protected amino acids to a growing peptide chain, especially by the method of Merrifield as reported, for example, in *Journal of American Chemical Society*, 85, pp. 2149–2145 (1963). These derivatives are also useful for preparing polypeptides by classical techniques as taught in, for example, M. Bodanszky, et al., *Peptide Synthesis*, Interscience, second edition, 1976 (hereinafter "Bodanszky").

An advantage of the method of this invention is that a yield in excess of 90 percent of the theoretically calculated amount of the alpha-epsilon amino-protected L-lysine can be harvested. These harvested crystals have an L-isomer content of at least about 99.5 percent and have a relatively low D-isomer content, i.e., less than about 0.5 percent.

Still further benefits and advantages of the present invention will be apparent to those skilled in the art from the detailed description and the Examples that follow.

DETAILED DESCRIPTION OF THE INVENTION

Crystalline amino-protected L-lysine having both its alpha-amino functional group and its epsilon-amino functional group protected with an amino-protective group can be prepared by the method of this invention without losing a substantial amount of the protective groups. For convenience, an amino-protected L-lysine having both its alpha-amino and its epsilon-amino group protected is interchangeably referred to herein as alpha-epsilon amino-protected L-lysine. For the same reason, alpha-tert-butyloxycarbonyl-epsilon-benzyloxy-carbonyl-L-lysine is referred to herein as N-alpha-t-BOC-N-epsilon-Z-L-lysine.

A crystalline N-alpha-t-BOC-N-epsilon-Z-L-lysine having a melting point range of about 71° C. to about 76° C. prepared by one method aspect of this invention is further characterized by the representative X-ray diffraction data in Table I of Example 1 and its corresponding line profile shown in FIG. 1.

Figure 2:
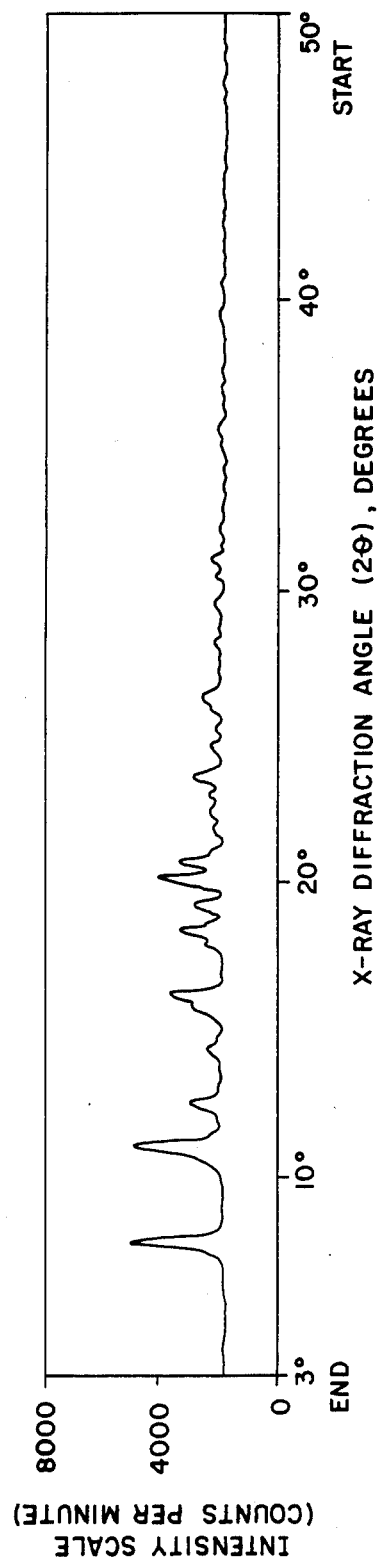
FIG. 2 sets forth the X-ray diffraction pattern in line profile for crystalline alpha-tertbutyloxycarbonyl-epsilon-benzyloxycarbonyl-L-lysine of Example 7 herein as prepared by a method of this invention.

A relatively high-purity crystalline N-alpha-t-BOC-N-epsilon-Z-L-lysine prepared by another method aspect of this invention having a melting point range of about 73° C. to about 78° C. is further characterized by the representative X-ray diffraction data shown in Table IV of Example 7 and its corresponding line profile shown in FIG. 2.

The amino-protective groups on the alpha amino and epsilon amino functional groups of L-lysine may be the same or different. However, these groups should be stable to removal by the process steps of the method of this invention, while still being readily removable under preparative conditions chosen for their subsequent use in manufacturing polypeptides.

A number of methods for reacting L-lysine with an amino-protective group-adding reagent for purposes of blocking one or more of its amino functional groups to protect it from peptide bond reactive reagents until a later stage are well known in the art. The reagents employed to introduce amino protecting groups are referred herein as "amino-protective group-adding reagents". A discussion of these reagents and suitable protective groups can be found in, for example, *Protective Groups in Organic Chemistry*, J. F. W. McOmie, ed., Plenum Press, N.Y., 1973, and in the *Concise Encyclopedia of Biochemistry*, Walter de Gruyter, N.Y., 1983, the pertinent portions of which are incorporated herein by reference.

Typically, any of the functional amine groups of unprotected L-lysine can be protected or blocked by reacting with an oxycarbonyl compound containing an amino-protective group or urethane type protecting group having the formula R—O—CO—, wherein R is any moiety which will prevent the amino group from entering into subsequent coupling reactions and which can be removed without destruction of the L-lysine molecule.

Thus, R can be a straight or branched chain $C_1$ to $C_{10}$ alkyl group which may be unsaturated and can be halo- or cyano-substituted; a $C_6$ to $C_{15}$ aryl group; a $C_5$ to $C_8$ cycloalkyl group; a $C_7$ to $C_{18}$ aralkyl group; a $C_7$ to $C_{18}$ alkaryl group; or a heterocyclic group, e.g., isonicotinyl. The aryl, aralkyl and alkaryl moieties can also be further substituted as by one or more $C_1$ to $C_4$ alkyl groups.

Preferred groupings for R include tertbutyl, tert-amyl, tolyl, xylyl and benzyl. Highly preferred specific amino-protecting groups include benzyloxycarbonyl; substituted benzyloxycarbonyl wherein the phenyl ring is substituted by one or more halogens, e.g., Cl or Br, nitro, lower alkoxy, e.g., methoxy, or lower alkyl; tert-butyloxycarbonyl, tert-amyloxycarbonyl; cyclohexyloxycarbonyl; vinyloxycarbonyl; adamantyloxycarbonyl; 2-(p-biphenylyl)isopropoxycarbonyl; and the like. Other aminoprotecting groups which can be used include isonicotinyloxycarbonyl, phthaloyl, p-tolylsulfonyl, formyl and the like.

As used herein, the term "halo" includes fluoro, chloro, bromo, and iodo, but chloro and bromo are preferred. The terms "lower alkyl" and "lower alkoxy" include, respectively, saturated aliphatic $C_1$ to $C_6$ hydrocarbons, such as methyl, ethyl, isopropyl, tert-butyl, n-hexyl, and the like, and the corresponding alkoxy groups, such as methoxy, ethoxy, isopropoxy, tert-butoxy, n-hexoxy, and the like. Methyl is the preferred lower alkyl and methoxy is the preferred lower alkoxy.

In a preferred embodiment of this invention, suitable amino-protecting groups include salts protecting the strongly-basic amino groups of L-lysine, or urethane-type protecting substituents, such as tert-butyloxycarbonyl, tert-amyloxycarbonyl and benzyloxycarbonyl moieties. It is preferred to utilize the tert-butyloxycarbonyl (t-BOC) moiety for protecting the alpha-amino group of L-lysine, and the benzyloxycarbonyl (Z) moiety for protecting the epsilon-amino group of L-lysine.

Methods for preparing alpha-epsilon amino-protected L-lysine are well known in the art. These methods typically employ as starting materials, an epsilon-amino protected L-lysine that is reacted with an amino-protective group-adding reagent to introduce an alpha amino-protecting group or alternately, an alpha-amino protected L-lysine that is reacted with an amino-protective group-adding reagent that introduces an epsilon protective group.

A description of the foregoing methods can be found in Bodanszky at pages 85–128; chapter 2 on laboratory techniques found in J. M. Stewart and J. D. Young, *Solid Phase Peptide Synthesis*, Second edition, Pierce Chemical Company, Rockford, IL, at pages 61–64 (1984); Schwyzer, R., et al., *Helv. Chim. Acta.*, 42, 2622 (1959); Moroder, L., et al., *Hoppe-Seylers Z. Physiol. Chem.*, 357, 1651–1653 (1976); Schnabel, E., *Ann. Chem.*, 702, 188–196 (1967); Perseo, G., et al., *Int. J. Peptide Protein Res.*, 21 227–230 (1983); U.S. Pat. No. 3,855,238 to Batesky, et al., and U.S. Pat. No. 3,609,164 to Miyoshi, et al., the pertinent disclosures of which are incorporated herein by reference.

Relatively pure amino-protected L-lysine derivates are substantially stable at room temperature for long periods of time. However, any traces of acid remaining in them from acidic extraction steps during their preparation will promote cleavage and removal of the amino-protective group, especially a t-BOC group, resulting in unprotected L-lysine. Consequently, alpha-epsilon amino-protected L-lysine derivatives useful as starting materials herein are preferably prepared from bases under alkaline conditions having pH values in the range of about 8.5 to 14, preferably in the range of about 9.5 to 13.5, to provide a water-soluble addition salt thereof.

The term "addition salt" denotes the amino acid formed as its corresponding salt from inorganic bases containing an alkali metal cation, such as sodium or potassium, or an alkali earth metal cation, such as calcium or magnesium, or from an organic tertiary amino base having a $pK_a$ value of about 9 to about 12.

Suitable tertiary amines include triethylamine ($pK_a$ 10.65), and those containing three lower alkyl ($C_1$–$C_6$) groups on an amino-nitrogen atom, such as trimethylamine ($pK_a$ 9.76), tri-n-propylamine ($pK_a$ 10.65), tri-n-butylamine ($pK_a$ 10.89) or the like; and heterocylic tertiary amines, such as N-ethylpiperidine ($pK_a$ 10.40), 4-dimethylaminopyridine ($pK_a$ 9.7), or the like.

Alternatively, commercially available non-crystalline alpha-epsilon amino-protected L-lysine can be used as the starting material in the method of this invention. Typically, such a non-crystalline alpha-epsilon amino-protected L-lysine is an oil-like or semi-solid amorphous mass.

To prepare a relatively high-purity, crystalline alpha-epsilon amino-protected L-lysine in a high yield, a solution containing the compound in relatively impure form is subjected to extraction, isolation, crystallization and, optionally, to further purification.

The present method comprises the following steps. A solution of relatively impure alpha-epsilon amino-protected L-lysine is provided in a substantially water-immiscible polar solvent for the L-lysine derivative. Preferably the polar solvent solution contains about 30 to about 40 weight percent of alpha-epsilon amino-protected L-lysine. The polar solvent solution is combined with an organic non-polar phase modifier that is miscible with the water-immiscible solvent, but is not a solvent for the L-lysine derivative, to provide an admixture (mother liquor) in which the solubility of the L-lysine derivative is decreased.

The water content of the polar solvent, as well as that of the produced mother liquor, is important. The water content in the mother liquor is maintained at no more than about 0.9 weight percent, preferably at no more than about 0.3 weight percent. If the water content of the resulting admixture (mother liquor) requires adjustment, it is subjected to drying.

Drying can be accomplished by utilizing a phase modifier that is capable of forming an azeotrope with water that boils below about 90° C. at 1 atmosphere pressure and then removing water from the mother liquor by azeotropic refluxing, preferably at a temperature in the range of about 70° C. to about 90° C.

Alternatively, drying can be accomplished by passing the mother liquor over drying agent, such as magnesium sulfate, sodium sulfate, calcium chloride, a molecular sieve, or the like.

The solubility of the alpha-epsilon amino-protected L-lysine in the relatively dry solution is reduced, in the presence of a nucleating agent, until the solution becomes supersaturated with respect to the alpha-epsilon amino-protected L-lysine present at about ambient room temperature. This reduction in solubility can be accomplished by the addition of aliquots of the phase modifier until crystals of the amino-protected L-lysine begin to form. Preferably, these additions are carried out in combination with a reduction in the temperature of the solution below its saturation point.

A nucleating agent is used to initiate crystallization. A suitable nucleating agent is a seed crystal of the same alpha-epsilon aminoprotected L-lysine or an inert nucleation promoter, such as powdered glass, glass rod stirrers and the like. Techniques for seeding are well-known in the art.

A nucleating seed crystal can be obtained, if desired, by the evaporative drying and crystallizing method as described hereinbelow in Example 1.

While in practicing the method of this invention crystallization can be carried out at about room temperature, higher yields are more reproducibly obtained at temperatures in the range of about 0° C. to about 10° C., preferably at about 0° C. to about 5° C.

It was found that the rate of crystallization was important for achieving a crystalline product rather than a non-crystalline mass. By monitoring the amount of L-lysine derivative dissolved in the supersaturated, nucleated solution (mother liquor), it was found that crystallization proceeded relatively quickly as the dissolved amount decreased from about 0.6 to about 0.3 milliequivalents per milliliter (meq/ml) over a period of about two to about three hours. The rate of crystallization then slowed and very little additional crystallization could be achieved unless incremental additions of aliquots of phase modifier were made.

The incremental addition of aliquots of the phase modifier, in the presence of nucleating agent is important for achieving relatively high yields. It was found that the rate at which the phase modifier was added also affected the quality of the crystallization. Too rapid an addition rate caused some oiling that resulted in a tacky semi-solid amorphous mass. A suitable rate of addition was found to be in the range of about 0.065–0.09 milliliters (ml) per minute per gram of theoretically calculated total yield. Incremental additions preferably are spaced at time intervals of about 5–10 minutes per addition over a total of 1.5 to 2 hours.

Monitoring the amount of alpha-epsilon amino-protected L-lysine dissolved in the mother liquor prior to the addition of further aliquot portions of phase modifier is also important for crystal quality. It was found that if the extent of crystallization had not proceeded sufficiently to lower the meq/ml of alpha-epsilon amino-protected L-lysine to less than 0.5, the addition of an additional aliquot portion of phase modifier caused the product to oil out, resulting in a gummy non-crystalline mass. Preferably, the foregoing level of crystallization in the nucleated admixture provides as a solid crystalline mass at least about 15 weight percent, preferably about 25 weight percent or more, of the alpha-epsilon amino protected L-lysine present. I.e., less than about 85–75 weight percent of alpha-epsilon amino-protected L-lysine present remains dissolved.

If the admixture is azeotropically refluxed to reduce its water content, the refluxed liquid admixture is cooled to at least about ambient temperature prior to adding an effective amount of nucleating agent to the cooling refluxed liquid admixture. Preferably, the nucleating agent is added at a temperature of about 10° C., and thereafter the temperature of the nucleated solution, having the reduced water content, is reduced further to a temperature in the range of about 0° C. to about 5° C.

In any event, the solubility of the alpha-epsilon amino-protected L-lysine is reduced until a solid crystalline phase separates out of the nucleated solution. The separated solid crystalline phase is then harvested.

Useful "substantially water-immiscible" polar solvents include liquid organic solvents that preferably form an azeotrope with water, and in which the alpha-epsilon amino-protected L-lysine is soluble. Preferably the solubility of the polar solvent in water at about 25° C. is no more than about 15 weight percent, and the solubility of water in the polar solvent is no more than about 5 weight percent. It is also preferred that any azeotrope that forms boils below about 90° C. at 1 atmosphere pressure.

The polar solvents useful herein preferably have a solubility parameter delta value of about 3.9 to about 4.7. The solubility parameter delta value is the energy of vaporization per unit volume, and is expressed as the square root of Joules per cubic meter $[(J/m^3)^{1/2}] \times 10^{-3}$. A discussion of solubility parameter delta values for various industrial solvents and their calculation is found in *Kirk-Othmer Encyclopedia of Chemical Technology*, Third Edition, 21, pages 377–387 (1983), the pertinent disclosures of which are incorporated herein by reference.

Suitable polar solvents for N-alpha-t-BOC-N-epsilon-Z-L-lysine, for example, include liquid lower $C_2$ to $C_5$ alkyl esters of $C_1$ to $C_2$ monocarboxylic acids, such as ethyl formate, ethyl acetate, n-propyl acetate, isopropyl acetate, n-butyl acetate, sec-butyl acetate, isobutyl acetate, and isoamylacetate. Ethyl acetate and isopropyl acetate are particularly preferred.

Other suitable polar solvents include $C_1$ to $C_2$ halogenated hydrocarbons, such as chlorinated methanes and chlorinated ethanes. Suitable chlorinated methanes include methylene chloride, chloroform and carbon tetrachloride. Suitable chlorinated ethanes include perchloroethylene, 1,1,2,2-tetrachloro-ethane, and the like. Methylene chloride and chloroform are particularly preferred.

A useful amount of polar solvent is about 2–3 parts by volume, preferably 2.5–2.7 parts by volume, per part by weight of the theoretically calculated total gram yield of alpha-epsilon amino-protected L-lysine.

The term "phase modifier" as used herein, denotes a non-polar organic liquid diluent that is miscible with the water-immiscible solvent but is not a solvent for the alpha-epsilon amino-protected L-lysine. The phase modifier preferably forms an azeotrope with water that boils at a temperature below about 90° C. at 1 atmosphere pressure. The solubility of the non-polar liquid in water is no more than about 0.01 weight percent at 25° C. and the solubility of water in the non-polar liquid at 25° C. is no more than about 0.05 weight percent.

A non-polar organic liquid useful herein as a phase modifier preferably has a solubility parameter delta value of about 3.4 to about 4.0. The phase modifier can be comprised of one or more non-polar organic liquids.

Liquid $C_5$ to $C_8$ aliphatic and cycloaliphatic hydrocarbons are preferred as phase modifiers, with liquid $C_6$ to $C_7$ aliphatic hydrocarbons being particularly preferred. Suitable aliphatic hydrocarbons include n-pentane, n-hexane, cyclohexane, methyl cyclopentane, n-heptane, n-octane, isooctane and mixtures thereof. A particularly preferred phase modifier is a mixture of hexanes that contains more than 94 volume percent n-hexane in methyl cyclopentane, as assayed by gas chromatography, has a moisture content of not more than 0.01 weight percent, and a boiling range of about 67° C. to about 72° C. at 1 atmosphere pressure. This mixture is interchangeably referred to hereinafter by the terms, "hexanes" and "mixed hexanes".

A useful amount of phase modifier is about 1.5–2.5 parts by volume, preferably about 1.9–2.1 parts by volume, of the theoretically calculated total gram yield of alpha-epsilon amino-protected L-lysine.

The moisture or water content of the utilized materials and of the refluxing medium, can be determined by the well-known Karl Fischer Titrational Method using Karl Fischer Reagents. Water content of the water-immiscible organic solvent phase of no more than about 0.9 percent is important for obtaining crystallized alpha-epsilon amino-protected L-lysine. It has been found that when the water or moisture content is above this level, crystallization does not take place. Rather, a non-crystalline oil-like or an amorphous semi-solid mass is obtained.

The terms "azeotropic mixture", "azeotrope" and grammatical variations thereof are used interchangeably for their commonly understood meaning describing a liquid mixture that has a constant boiling point at a particular composition. A brief discussion of azeotrope systems can be found in the *Encyclopedia of Chemistry*, Fourth Ed., D. M. Considine ed., Van Nostrand Reinhold, 1984.

A preferred method aspect of this invention comprises the following steps for preparing crystalline alpha-t-BOC-epsilon-Z-L-lysine.

A water-containing solution of an addition salt of N-alpha-t-BOC-epsilon-N-Z-L-lysine prepared from an inorganic base having an alkali metal cation is provided, and is admixed with a water-immiscible polar solvent, preferably ethyl acetate. The resulting admixture is acidified with a mineral acid to convert the dissolved addition salt to the free acid form. Acidification is preferably carried out at a temperature in the range of about 0° C. to about 5° C. The acidified mixture is agitated to extract the free acid form of L-lysine derivative into the polar solvent phase which is then separated from the water-containing phase.

The concentration of the extracted free acid form of L-lysine derivative in the polar solvent phase is adjusted to about 40 weight percent based on the volume of the solvent by distillation at a temperature in the range of about 70° C. to about 90° C. under conditions of atmospheric pressure.

The solubility of the free acid form of L-lysine derivative in the resulting concentrated extract is reduced by cooling the distilled extract to about 50° C. and admixing therein an aliquot of liquid non-polar phase modifier, preferably n-heptane or a mixture of hexanes as described above. The amount of phase modifier added is sufficient to reduce solubility so that the admixture becomes supersaturated with the L-lysine derivative at about ambient temperature.

The resulting liquid admixture is then azeotropically refluxed at a temperature in the range of about 70° C. to about 90° C., preferably about 80° C. to about 90° C., to dry the admixture to a water content of no more than 0.9 weight percent, preferably to 0.3 weight percent.

This refluxed, dry admixture is thereafter cooled to a temperature in the range of about 0° C. to about 5° C. An effective amount of nucleating agent is added to the cooling admixture when the temperature thereof is no more than about 10° C.

The solubility of the free acid form in the cooled nucleated admixture is reduced by adding further aliquots of phase modifier in an amount sufficient to form a solid crystalline material. The aliquot portions are added in incremental amounts at a rate sufficient to maintain the temperature in the range of about 0° C. to about 5° C. The resulting formed solid crystalline material is then harvested and can be purified further, if desired.

Crystalline N-alpha-t-BOC-N-epsilon-Z-L-lysine of relative high purity prepared by the method of this invention is typically a white crystalline powder or solid having a melting point of about 73° C. to about 78° C., a specific rotation at 20° C. at the sodium D line of −12.0° to −14.0°, determined at a concentration of 250 milligrams in 25 milliliters of 97 percent formic acid, an optical purity of not less than 99.5 percent, and a moisture content (Karl Fischer) of not more than about 0.2 percent. The crystalline compound obtained assays at about 98.5 to about 100 percent purity as determined by titrating the admixture as described in Example 2 hereinbelow. Not more than about 0.2 percent of unprotected L-lysine is present, based on a thin layer chromatography determination.

The crystalline form of the compound of this invention has been deposited with the American Type Culture Collection (ATCC) and has been assigned ATCC Accession Number 40,230.

For the acidification step described above, any mineral acid having a $pK_a$ value of about 4.5 or lower is suitable. Such mineral acids include hydrochloric, sulfuric, and phosphoric acid. Hydrochloric acid is particularly preferred. A useful concentration of mineral acid for the acidification step is about 1N to 2N, preferably about 2N, to minimize the amount of added water.

For acidification of the admixture, the acid must be strong enough to lower the pH value of the admixture enough to completely convert the addition salt of N-alpha-t-BOC-N-epsilon-Z-L-lysine to the free acid form without using an unreasonable quantity of acid and without removing either the alpha-amino or epsilon-amino protective group therefrom. The pH values suitable for this purpose are in the range of about 1 to about 4, preferably about 1.5 to about 2.5. A pH value of about 2 is particularly preferred.

Hydrochloric acid at a concentration of 12N is not recommended, because it is difficult to control its addition rate during the acidification step and may overshoot the desired final pH range; it is also believed that such a highly concentrated acid present in localized amounts during acidification may remove the t-BOC group from the alpha-amino group.

The acidification step converts any water-soluble addition salts of unprotected L-lysine present in the admixture to unprotected L-lysine in its free acid form, which remains soluble in water. However, the acidification treatment also converts the addition salt of alpha-epsilon amino-protected L-lysine to the free acid form which is not soluble in water. This alpha-epsilon amino-protected L-lysine can thus be extracted and isolated from the relatively more water-soluble forms of the unprotected L-lysine.

Traces of mineral acid remaining in the extract from the acidification can be removed along with other water-soluble impurities by admixing a saturated salt solution therein and then isolating the extract from the resulting salt wash. Suitable saturated salt solutions can be prepared using sodium chloride, sodium sulfate, potassium chloride, potassium sulfate, and the like. A particularly preferred saturated salt solution is aqueous 25 weight percent sodium chloride solution.

The resultant admixture has a substantially neutral pH value. Neutrality is important to minimize the possibility of removing the aminoprotective groups from the amino-protected L-lysine. A "substantially neutral" pH value for the present purposes is in the range of about 6 to about 8.

Persons skilled in the art will recognize that organic acids, such as acetic acid, citric acid, succinic acid, tartaric acid or the like can be employed in the place of the mineral acid in the acidification step. However, no procedural or economic advantage is obtained thereby because greater amounts of organic acid are needed to obtain the preferred pH value.

The method aspect of this invention can further include a purification step of polish filtering, prior to the addition of the nucleating agent, to remove traces of the saturated salt solution, if any, remaining in the above extract from the salt wash step. The presence of traces of salt will result in the formation of salt crystals, e.g., sodium chloride, after the azeotropic drying step.

The term "polish filtering" and grammatical variations thereof describe the filtering of the neutralized liquid mixture to remove solid impurities therefrom. Typically, this is carried out by vacuum filtering the liquid mixture through either a Buchner funnel covered with paper, a sintered glass funnel or the like. Other filtration techniques for removing solids from a liquid may be employed. The resulting polished filtrate is thereafter returned to the crystallizing vessel.

The method of this invention as described above in essence effects a single stage extraction of alpha-epsilon amino-protected L-lysine. However, the extraction step can also be carried out in multiple stages by cross-current or counter-current flow arrangements.

It has been found that relatively high-purity crystalline alpha-epsilon amino-protected L-lysine, and particularly crystalline N-alpha-t-BOC-N-epsilon-Z-L-lysine, can be prepared in the foregoing manner. Surprisingly, neither of the amino-protective groups was removed during the acidification step of the present method so long as traces of acid were removed with a salt wash after the extraction of the free acid form. While prolonged exposure of an amino-protected L-lysine to acidic conditions usually results in the removal of amino-protective groups, by practicing the method of this invention unprotected L-lysine was not detected in the acidified admixture unless its pH value was below 1.0.

DETAILED DESCRIPTION OF DRAWINGS

FIG. 1 is the qualitative line profile of the X-ray diffraction pattern of N-alpha-t-BOC-N-epsilon-Z-L-lysine prepared as described in Example 1 hereinbelow. The Figure is a line profile of the intensity scale in counts per second of the reflected X-ray beam expressed as a function of X-ray diffraction angle, $2\theta$, scanned at a rate of 2 degrees per minute over an angular range starting at 50 degrees and ending at 3 degrees. This X-ray profile was obtained using a Rigaku Miniflex Powder X-Ray Diffractometer, and a copper radiation source measured as Cu Kα.

FIG. 2 is the qualitative line profile of the X-ray diffraction pattern of N-alpha-t-BOC-N-epsilon-Z-L-lysine prepared as described in Example 7 hereinbelow similarly expressed as in FIG. 1. The invention is further illustrated by the examples which follow.

EXAMPLE 1

Preparation of Nucleating Seed Crystal

Seed crystals of alpha-tert-butyloxycarbonylepsilon-benzyloxycarbonyl-L-lysine were prepared from an amorphous N-alpha-t-BOC-N-epsilon-Z-L-lysine by the following procedure.

A solution of 0.17 moles of N-alpha-t-BOC-N-epsilon-Z-L-lysine in ethyl acetate was provided by the reaction of N-epsilon-Z-L-lysine with di-t-butyldicarbonate in a procedure similar to that of Perseo, R., et al. (hereafter Perseo et al.), *Int. J. Peptide Protein Res.*, 21, 227–230 (1983).

Initially, attempts were made at obtaining crystals by the addition of hexanes and chilling the admixture, which only resulted in the product coming out of solution as an oil. After several such unsuccessful attempts, the solvents were removed in vacuo to provide 75.6 grams of a light yellow oil.

This oil was placed in a round-bottomed flask and the sides of the flask were scratched to initiate crystallization. After standing approximately three weeks at room temperature and being periodically nucleated in the foregoing manner, the oil was substantially crystallized.

A portion of the crystals was removed and slurried in 30 ml of 33 volume percent ethyl acetate in hexanes. A first crop was harvested by filtration, washing the obtained crystals with 25 volume percent ethyl acetate in hexanes, and drying them to provide 3.75 grams. A second crop of 8.10 grams crystals was harvested by adding 90 ml of 33 percent ethyl acetate in hexanes to the crystals remaining in the flask and filtering the suspended crystals. The remaining large crystalline particles which could not be suspended were harvested and dried to give 38.01 grams for a total crop yield of 49.86 grams representing a yield of about 77.2 percent.

The second crop was judged slightly impure due to the presence of some oil as reflected by a slightly lower melting point range of about 71.8° C. to about 76.0° C. Nonetheless, in spite of this, it was shown to be crystalline by its circular birefringance when viewed with a polarizing microscope, and by its X-ray diffraction pattern shown in Table I below.

TABLE I

| 2θ | dA° | I/I$_o$ |
|---|---|---|
| \multicolumn{3}{|c|}{X-Ray Diffraction Data[a]} |
| 7.95 | 11.182 | 0.50 |
| 11.25 | 7.8585 | 1.00 |
| 12.60 | 7.0193 | 0.23 |
| 16.00 | 5.5345 | 0.18 |
| 16.35 | 5.4169 | 0.34 |
| 18.60 | 4.7663 | 0.32 |
| 19.50 | 4.5483 | 0.20 |
| 20.40 | 4.3496 | 0.39 |
| 20.95 | 4.2367 | 0.27 |

TABLE I-continued

| 2θ | dA° | I/I$_o$ |
|---|---|---|
| \multicolumn{3}{|c|}{X-Ray Diffraction Data[a]} |
| 23.85 | 3.7277 | 0.21 |

[a]In the Table, 2θ is the diffraction angle of the reflected beam calculated according to Bragg's Law, dA° is the interplanar spacing distance in intensity expressed in counts per second of the observed intensity (I) for a particular reflection to the true absolute incident intensity of the strongest separated reflection (I$_o$) occurring in the diffraction pattern. The foregoing representative X-ray diffraction data were obtained using a Rigaku Miniflex Powder X-Ray Diffractometer, and as a radiation source, copper measured as Cu Kα radiation wavelength of lambda = 1.542 Angstroms.

The corresponding qualitative line profile for the X-ray diffraction pattern of the seed crystals obtained is shown in FIG. 1.

EXAMPLE 2

Monitoring of Crystallization

To determine the extent of crystallization of N-alpha-t-BOC-N-epsilon-Z-L-lysine in the following Examples, an aliquot of nucleated solution (about 5 ml) was sampled just prior to the step of adding additional aliquots of phase modifier. The sampled portion was pressure filtered, through a non-sterile Gelman disposable filter of 0.45 micron pore size (Acrodisc®-CR) or equivalent using a syringe.

To obtain an accurate representation of the degree of crystallization, the filtrate was not diluted either by washing the filter cake or by concentrating the volume by filtering under vacuum. The filtrate was collected in a glass beaker and was assayed for the milliequivalents (meq) of N-alpha-t-BOC-N-epsilon-Z-L-lysine present by the following titration method.

A portion of the filtrate (about 1 ml) was pipetted and transferred to a titration flask containing methanol (100 ml) of high performance liquid chromatography (HPLC) grade. The sample was titrated with a titrant solution of aqueous tetrabutyl ammonium hydroxide (0.1N) to the endpoint using an automatic titrator unit (Metrohm E 536).

For comparison, a corresponding blank volume of methanol was similarly titrated and the meq of N-alpha-t-BOC-N-epsilon-Z-L-lysine present per ml volume of nucleated solution sampled was calculated as follows:

$$\frac{(V - B)(N)}{S} = \text{meq/ml N—alpha-t-BOC—N—epsilon-Z—L—lysine in solution}$$

where V=ml volume of sample titrated, B=blank volume, N=normality of the titrant solution, and S=ml volume of sample titrated. Two titration determinations were made per sampling and an average value calculated.

The extent of crystallization taking place in the nucleated solution was determined periodically in the manner described above until an average value of less than 0.5 meq/ml was obtained, prior to proceeding with the addition of a second aliquot of phase modifier.

Similarly, the extent of crystallization taking place after the second addition of phase modifier was determined at periodic intervals. The foregoing procedure was followed, except that a large portion (8–10 ml) of chilled solution was sampled until an average value of less than 0.02 meq/ml was obtained, prior to proceeding with the harvesting step.

The filter cake obtained from each of the above filtration steps from each of the sampled portions was retained and combined with the crystalline N-alpha-t-BOC-N-epsilon-Z-L-lysine filter cake obtained in the filtration step and purified therewith.

EXAMPLE 3

Preparation of Crystalline alpha-tert-Butyloxycarbonylepsilon-Benzyloxycarbonyl-L-Lysine This example illustrates the method of this invention in preparing a relatively high-purity crystalline N-alpha-t-BOC-N-epsilon-Z-L-lysine in relatively high yields, i.e., in excess of above 90 percent of theoretically calculated yield, and having an optical purity of about 99.5 percent as determined by the chiral gas chromatography method.

A crude, water-containing solution was provided containing approximately 129 grams (0.34 moles) of N-alpha-t-BOC-N-epsilon-Z-L-lysine in the form of its water-soluble sodium salt generally following the procedure described in Perseo et al. This aqueous solution (680 ml) was transferred to a flask equipped with a mechanical agitator, thermometer, addition funnel and bottom outlet.

The N-alpha-t-BOC-N-epsilon-Z-L-lysine present was extracted from the solution by adding ethyl acetate (340 ml) to the flask with stirring. While maintaining stirring, the resulting admixture was then chilled to a temperature in the range of about 0° C. to about 5° C.

N-alpha-t-BOC-N-epsilon-Z-L-lysine was subsequently extracted from the resulting chilled admixture by acidifying it to a pH value of about 2, determined with a pH meter standardized at a pH value of 4. The procedure for acidification consisted of gradually adding to the chilled admixture relatively small incremental amounts of a hydrochloric acid solution (2N) until a pH value of 2.0 was achieved (a volume of 534 ml was added). The rate at which the acid solution was added was relatively slow in order to maintain the temperature of the mixture in the range of about 0° C. to about 5° C., and to allow time for the escape of any carbon dioxide gas present in the solution. The addition of the total amount of acid, therefore, took place over a period of about 45 minutes.

The cooled and acidified solution was stirred for a period of about 30 minutes. This period was sufficiently long to convert the water-soluble sodium salt of N-alpha-t-BOC-N-epsilon-Z-L-lysine present to its corresponding water-insoluble acid form, but was not sufficiently long to remove either of the amino-protective groups therefrom. The stirring was then stopped, and the water-rich phase was allowed to separate from the water-immiscible, ethyl acetate-rich phase containing water-insoluble N-alpha-t-BOC-N-epsilon-Z-L-lysine.

The water-rich phase was separated and discarded. The obtained ethyl acetate-rich phase was then washed to remove water-soluble impurities therefrom. To that end, aqueous, saturated sodium chloride solution (200 ml) was mixed therein. The produced substantially neutral admixture was stirred for a period of about 30 to 45 minutes, which was sufficient to remove water-soluble impurities. The stirring was then stopped and an aqueous phase was allowed to separate out.

The aqueous phase was then separated and discarded. The flask was fitted with a distilling head column, a water-cooled condenser, and a distillate collection vessel. Crystallization of the N-alpha-t-BOC-N-epsilon-Z-L-lysine from the washed ethyl acetate-rich phase proceeded as follows.

The washed ethyl acetate-rich phase was distilled at a temperature in the range of about 70° C. to about 90° C. under conditions of atmospheric pressure and using steam heat for a period of time sufficient to concentrate the volume of the ethyl acetate-rich phase to a vessel residue of about 320 to about 330 ml. This residue represented a concentration of approximately 0.4 grams per milliliter of N-alpha-t-BOC-N-epsilon-Z-L-lysine in ethyl acetate.

The concentrated vessel residue was allowed to cool to about 50° C., and to the cooled residue was added a first aliquot of mixed hexanes (254 ml) as a phase modifier. This volume represented a ratio of two parts by volume of hexanes per part of calculated gram yield of N-alpha-t-BOC-N-epsilon-Z-L-lysine. This first addition reduced the solubility of the N-alpha-t-BOC-N-epsilon-Z-L-lysine in the newly obtained ethyl acetate-hexanes admixture. The admixture turned cloudy as the N-alpha-t-BOC-N-epsilon-Z-L-lysine partially crystallized.

The flask was then fitted with a Dean-Stark distilling receiver and a water-cooled reflux column. The obtained ethyl acetate-hexanes admixture was then azeotropically refluxed for a period of one hour at a refluxing temperature in the range of about 80° C. to about 90° C. for a period of time sufficient to provide a substantially anhydrous refluxing medium. During refluxing, the initially cloudy admixture turned clear.

The admixture was then cooled to a temperature of 50° C. and the vessel residue was sampled for moisture content by the well-known Karl Fischer Titration Method. Immediately after sampling, the reaction mixture was again reheated to continue refluxing. This procedure of sampling for moisture and reheating for reflux was repeated at periodic intervals until the admixture was determined to be substantially anhydrous, i.e., have a moisture value of no more than 0.3 percent by weight, at which point refluxing was stopped.

The obtained, substantially anhydrous admixture was then cooled to ambient temperature (about 20° C. to about 25° C.), and the Dean-Stark receiver was removed. The contents of the receiver were separated and the ethyl acetate-hexanes phase was returned to the admixture in the flask.

The admixture was further cooled in an ice bath to a temperature of about 10° C. At this temperature, the admixture was nucleated with 1–4 grams (based on 1–3 percent of theoretical yield) of seed crystals of N-alpha-t-BOC-N-epsilon-Z-L-lysine pzrepared as described in Example 1.

The produced nucleating solution was then chilled further to a temperature in the range of about 0° C. to about 5° C., and allowed to crystallize under stirring agitation for a period of 3 hours while maintaining the temperature thereat. The extent of crystallization was determined after this period by sampling the nucleated solution and by titrating for the amount of N-alpha-t-BOC-N-epsilon-Z-L-lysine remaining dissolved by the monitoring method described in Example 2, above.

When the average meq/ml value obtained by titration showed that the nucleated solution contained less than about 0.45 meq/ml of N-alpha-t-BOC-N-epsilon-Z-L-lysine dissolved therein, additional aliquots of hexanes at a temperature of about 0° C. to about 5° C. were added slowly with stirring agitation to the nucleated solution in incremental amounts of about 25 ml or continuously over a period of 1.5 to 2 hours until a total volume of 1050 ml of mixed hexanes was admixed therein. This addition provided a chilled slurry containing a crystalline solid material.

The chilled slurry was stirred for an additional hour, at which point the extent of N-alpha-t-BOC-N-epsilon-Z-L-lysine that crystallized out was determined by the monitoring method as hereinbefore described. This determination was periodically repeated until the nucleated solution was found to contain less than about 0.02 meq/ml of N-alpha-t-BOC-N-epsilon-Z-L-lysine.

Thereafter, the N-alpha-t-BOC-N-epsilon-Z-L-lysine crystals were recovered by filtration. The obtained filtrate was recycled and used to wash forward the contents of the flask so as to collect substantially all the crystals of N-alpha-t-BOC-N-epsilon-Z-L-lysine in the filter cake.

The filter cake was washed with hexanes (200 ml) at a temperature of about 0° C. to about 5° C. This volume represented a ratio of about 1.5 to about 1.75 parts by volume of hexanes to one part by weight of the filter cake. The obtained crystals were first allowed to dry in air by drawing air through the filter cake (using vacuum) for a period of about an hour, and were then dried under vacuum in an oven set at ambient temperature of about 20°-25° C. for a period of about 16 to about 20 hours.

The resulting product was a white crystalline powder. It was identified as N-alpha-t-BOC-N-epsilon-Z-L-lysine by thin layer chromatography, melting point, HPLC, infrared analysis, and by its X-ray diffraction pattern, which was substantially the same as that of the original seed crystals prepared in Example 1. The yield was 118.4 grams, representing 93.1 percent of theoretically calculated yield. The purity of alpha-epsilon-amino-protected L-lysine crystals was determined to be 99.5 percent. The presence of the D-isomer was determined to be less than 0.5 percent of the product by chiral gas chromatography method.

The melting point of the crystalline compound was about 73° C. to about 78° C., and the specific rotation at 20° C. at the sodium D line was −12.0° to −14.0° at a concentration of 10 milligrams per milliliter in N,N-dimethylformamide.

EXAMPLE 4

Preparation of Crystalline alpha-tert-Butyloxycarbonyl-epsilon-Benzyloxycarbonyl-L-Lysine This example illustrates the crystallization of N-alpha-t-BOC-N-epsilon-Z-L-lysine prepared by the method of this invention.

The procedure of Example 3 was followed, except that the extent of N-alpha-t-BOC-N-epsilon-Z-L-lysine crystallization was monitored in the chilled admixture after the addition of the first aliquot of hexanes and no second aliquot of hexanes was utilized for the purpose of this Example. The results are charted in Table II below, for a period of over 24 hours from the time of seeding with the nucleating crystal as a function of titrated meq/ml in the filtrate.

TABLE II

| Analysis No. | Degree of Crystallization | |
|---|---|---|
| | Hours Elapsed From Time of Seeding | Meq/ml N—alpha-t-BOC-N—epsilon-Z-L-lysine in Filtrate |
| 1. | zero (initial concentration) | 0.596 meq/ml |
| 2. | 0.5 hour | 0.586 meq/ml |
| 3. | 1.0 hour | 0.582 meq/ml |
| 4. | 1.5 hours | 0.588 meq/ml |
| 5. | 2.0 hours | 0.563 meq/ml |
| 6. | 2.5 hours | 0.503 meq/ml |
| 7. | 3.0 hours | 0.344 meq/ml |
| 8. | 3.5 hours | 0.298 meq/ml |
| 9. | 26.5 hours | 0.297 meq/ml |

The foregoing data show that crystallization of N-alpha-t-BOC-N-epsilon-Z-L-lysine proceeded relatively quickly when its concentration in the mother liquor (filtrate) was about 0.6 to about 0.3 meq/ml. Thereafter very little additional crystallization could be achieved in the absence of further additions of the phase modifier.

EXAMPLE 5

Preparation of Crystalline alpha-tert-Butyloxycarbonyl-epsilon-Benzyloxycarbonyl-L-Lysine The procedure of Example 3 was followed except that all amounts of materials used were increased for preparation of a 2.1 mole amount N-alpha-t-BOC-N-epsilon-Z-L-lysine, and the concentrated ethyl acetate phase obtained after the distillation step was polish filtered to remove particulate sodium chloride present prior to proceeding with the addition of the phase modifier. The quantities of ethyl acetate and hexanes were also increased while maintaining unchanged the volumetric ratio of one to another.

The polish filtering procedure employed in this example comprised the steps of transferring the concentrated ethyl acetate-rich phase to a sinteredglass Buchner funnel and filtering it under vacuum, after which the ethyl acetate-rich phase was returned to the original crystallizing vessel which had been rinsed clean of solids.

The product obtained was a white crystalline powder that was identified by its X-ray diffraction pattern as N-alpha-t-BOC-N-epsilon-Z-L-lysine and was obtained in a yield of 92.5 percent of theoretically calculated yield. The optical purity of the product was found to be greater than 99.5 and was 99.9 percent pure based on its melting point range of about 73° C. to about 78° C.

EXAMPLE 6

Preparation of Crystalline alpha-tert-Butyloxycarbonyl-epsilon-benzyloxycarbonyl-L-Lysine and the Effect of Water Content This example illustrates the relationship of water content of the mother liquor to crystallization. A series of seven different runs were carried out following the procedure of Example 3, except for the variation in drying the mother liquor to the water content shown in Table III, below, prior to nucleating it.

For each of the runs, ethyl acetate was used as the polar solvent for the N-alpha-t-BOC-N-epsilon-Z-L-lysine at a volume of 3.46 ml per gram of theoretically calculated yield of the L-lysine derivative at the point where the phase modifier was added as a 2.35 ml aliquot per gram of theoretically calculated yield of product.

In runs 1-4, n-heptane was used as the phase modifier, and in runs 5-7, the hexanes, as described above, were the phase modifier. The mother liquor was constituted by the obtained admixture of the polar solvent and the phase modifier.

TABLE III
Effect of Water Content on Crystallization

| Run No. | Drying Procedure | Phase Modifier | Weight - % Water In Mother Liquor | Crystallization |
|---|---|---|---|---|
| 1 | A | n-heptane | 0.97 | no |
| 2 | B | n-heptane | 0.26 | yes |
| 3 | C | n-heptane | 0.28 | yes |
| 4 | C | n-heptane | 0.24 | yes |
| 5 | A | hexanes | 1.17 | no |
| 6 | B | hexanes | 0.11 | yes |
| 7 | D | hexanes | 0.15 | yes |

Drying procedure A: The ethyl acetate solution was refluxed for one hour using a Dean-Stark distilling receiver to trap the water prior to adding the phase modifier.

Drying procedure B: The ethyl acetate-phase modifier admixture was azeotropically refluxed for one hour using a Dean-Stark distilling receiver.

Drying procedure C: The ethyl acetate solution was distilled to a volume representing a ratio of 3.46 parts by volume per gram of theoretically calculated yield of L-lysine derivative, phase modifier was then admixed therein and the admixture was azeotropically refluxed for one hour using a Dean-Stark distilling receiver to remove the water.

Drying procedure D: The ethyl acetate solution was distilled to a volume representing a ratio of 3.46 parts by volume per gram of theoretically calculated yield of L-lysine derivative, then admixed with the phase modifier and dried over anhydrous magnesium sulfate. The magnesium sulfate was removed by filtration before the nucleating seed crystal was added.

The foregoing results show that the removal of water in the mother liquor below the level of about 0.9 weight percent is important for crystallization. The results also illustrate that the water content of the mother liquor can be reduced by subjecting it to drying by either azeotropic refluxing or by using a drying agent.

EXAMPLE 7
Large-scale Preparation of Crystalline alpha-tert-Butyloxycarbonyl-epsilon-benzyloxycarbonyl-L-Lysine Alpha-t-BOC-epsilon-Z-L-Lysine was prepared in a Pilot Plant on a 69.2 mole scale following the procedure of Example 3, except that all the material amounts were increased proportionately and the concentrated ethyl acetate phase obtained after the distillation step was polish filtered generally following the procedure described in Example 5.

The crystalline product was obtained in a yield of 94.7 percent of theoretically calculated yield, and in 100 percent purity as determined by HPLC and titrimetric method. The optical purity was greater than 99.5% and the compound had a melting point range of about 74° C. to about 76° C. The X-ray diffraction pattern for the crystals was substantially identical to that of the original seed crystals prepared in Example 1 as shown by the data in Table IV below:

TABLE IV

| X-Ray Diffraction Data[b] | | |
|---|---|---|
| $2\theta$ | dA° | $I/I_o$ |
| 7.95 | 11.182 | 1.00 |
| 11.30 | 7.8273 | 0.91 |
| 12.75 | 6.9371 | 0.32 |
| 16.10 | 5.5004 | 0.35 |
| 16.40 | 5.4004 | 0.57 |
| 18.65 | 4.7537 | 0.50 |
| 19.50 | 4.5483 | 0.28 |
| 20.45 | 4.3391 | 0.71 |
| 21.00 | 4.2267 | 0.51 |
| 23.90 | 3.7200 | 0.32 |

[b]See footnote (a) of Table I in Example 1.

The corresponding qualitative line profile for the X-ray diffraction pattern of the crystals obtained in the pilot plant scale up are shown in FIG. 2. A comparison of the X-ray diffraction pattern of the crystals obtained with those of crystals prepared on a laboratory scale in Examples 3, 4 and 5 showed them to be substantially the same. The X-ray pattern of these crystals was judged more representative of the relative intensities of crystals having a relatively high-purity than that of the seed crystals obtained in Example 1, based on the higher melting point range of the crystals prepared by the method of this Example.

The present invention has been described with respect to preferred embodiments. It will be apparent to those skilled in the art that modifications and/or variations of the disclosed compositions and methods can be made without departing from the scope of the invention set forth herein.

What is claimed is:

1. Crystalline alpha-tert-butyloxycarbonyl-epsilon-benzyloxycarbonyl-L-lysine.

2. The alpha-tert-butyloxy-carbonyl-epsilon-benzyloxycarbonyl-L-lysine in accordance with claim 1 and having a melting point in the range of about 71° C. to about 78° C.

3. A crystalline alpha-tert-butyloxycarbonyl-epsilon-benzyloxycarbonyl-L-lysine having the X-ray diffraction profile of FIG. 2.

4. A method for preparing crystalline alpha-tert-butyloxycarbonyl-epsilon-benzyloxycarbonyl L-lysine which comprises the steps of providing a solution of alpha-tert-butyloxycarbonyl-epsilon-benzyloxycarbonyl L-lysine in a substantially water-immiscible polar solvent therefor;

reducing the solubility of the alpha-tert-butyloxycarbonyl-epsilon-benzyloxycarbonyl L-lysine in said solution while maintaining the water content of the resulting mother liquor at no more than about 0.9 weight percent, in the presence of a nucleating agent, until the mother liquor becomes supersaturated with respect to the alpha-tert-butyloxycarbonyl-epsilon-benzyloxycarbonyl L-lysine present and a solid crystalline phase separates out from said mother liquor; and harvesting the separated solid crystalline phase.

5. A method for preparing crystalline alpha-tert-butyloxycarbonyl-epsilon-benzyloxycarbonyl L-lysine which comprises the steps of providing a water-containing solution of alpha-tert-butyloxycarbonyl-epsilon-benzyloxycarbonyl L-lysine in a substantially water-immiscible polar solvent therefor;

admixing said solution with a non-polar organic liquid phase modifier that is miscible with said water-immiscible solvent but is not a solvent for the alpha-tert-butyloxycarbonyl-epsilon-benzyloxycarbonyl L-lysine, said phase modifier being admixed in an amount sufficient to reduce the solubility of the alpha-tert-butyloxycarbonyl-epsilon-benzyloxycarbonyl L-lysine in the solution so that the solution becomes supersaturated at about ambient temperature;

refluxing the resulting liquid admixture at a temperature in the range of about 70° C. to about 90° C. until the water content of the liquid admixture is no more than about 0.9 weight percent;

thereafter cooling the refluxed liquid admixture to a temperature below the saturation point for the L-lysine present;

adding an effective amount of nucleating agent to the cooling refluxed liquid admixture when the temperature thereof is no more than about ambient temperature; and harvesting crystalline alpha-tert-butyloxycarbonyl-epsilon-benzyloxycarbonyl L-lysine from the cooled and nucleated liquid admixture.

6. The method according to claim 5, wherein the nucleating agent is a seed crystal of alpha-tert-butyloxycarbonyl-epsilon-benzyloxycarbonyl-L-lysine.

7. A method for preparing crystalline alpha-tert-butyloxycarbonyl-epsilon-benzyloxycarbonyl-L-lysine which comprises the steps of preparing a water-containing solution of an addition salt of alpha-tert-butyloxycarbonyl-epsilon-benzyloxycarbonyl-L-lysine;

admixing said solution with a water-immiscible polar solvent for alpha-tert-butyloxycarbonyl-epsilon-benzyloxycarbonyl-L-lysine in free acid form;

acidifying the resulting admixture to convert the dissolved addition salt of alpha-tert-butyloxycarbonyl-epsilon-benzyloxycarbonyl-L-lysine to the free acid form thereof;

agitating the acidified admixture to extract the free acid form into the polar solvent;

concentrating the extract by distillation at a temperature of about 70° C. to about 90° C. until the concentration of the free acid form in the polar solvent is adjusted to about 40 weight percent, based on the volume of the solvent;

cooling the concentrated extract to a temperature of about 50° C.;

reducing the solubility of the free acid form in the cooled extract by admixing said extract with a non-polar organic liquid phase modifier that is miscible with said polar solvent but is not a solvent for the alpha-butyloxycarbonyl-epsilon-benzylcarbonyl-L-lysine, said phase modifier being added in an amount sufficient to reduce the solubility of the free acid form in the resulting admixture so that the admixture becomes supersaturated at about ambient temperature;

refluxing the resulting liquid admixture at a temperature in the range of about 80° C. to about 90° C. until the water content of the liquid admixture is no more than about 0.9 weight percent, based on the volume of the liquid admixture;

thereafter cooling the refluxed liquid admixture to a temperature in the range of about 0° C. to about 5° C.;

adding an effective amount of nucleating agent to the cooling refluxed liquid admixture when the temperature thereof is no more than about 10° C.;

reducing the solubility of the free acid form in the cooled admixture having the reduced water content, in the presence of the nucleating agent, until a solid crystalline material is formed; and harvesting the formed solid crystalline material.

8. The method according to claim 7 wherein the addition salt is prepared from a base that is a member of the group consisting of inorganic bases containing an alkali metal cation, inorganic bases containing an alkali earth metal cation and organic tertiary amine bases having a $pK_a$ of about 9 to about 12.

9. The method according to claim 7 wherein the cation of the addition salt is a cation selected from the group consisting of sodium and potassium.

10. The method according to claim 7 wherein the polar solvent is ethyl acetate.

11. The method according to claim 7 wherein the admixture is acidified with a mineral acid selected from the group consisting of hydrochloric acid, phosphoric acid, and sulfuric acid, at a temperature in the range of about 0° C. to about 5° C.

12. The method according to claim 7, wherein the phase modifier is a liquid aliphatic or cycloaliphatic $C_5$ to $C_8$ hydrocarbon capable of forming an azeotrope with water that boils below about 90° C. at 1 atmosphere pressure and having a solubility parameter delta value of about 3.4 to about 4.0.

13. The method according to claim 12, wherein the phase modifier is a $C_6$ to $C_7$ aliphatic hydrocarbon.

14. The method according to claim 12, wherein the phase modifier is n-heptane.

15. The method according to claim 12 wherein the phase modifier is a mixture of hexanes, said mixture containing more than 94 volume percent of n-hexane in methyl cyclopentane, said mixture having a boiling point in the range of about 67° C. to about 72° C. at 1 atmosphere pressure.

16. The method according to claim 7 wherein the nucleating agent is a seed crystal of alpha-tert-butyloxycarbonyl-epsilon-benzyloxycarbonyl-L-lysine.

17. The method according to claim 7 wherein the solubility of the free acid form is reduced in the cooled admixture by admixing therein a further amount of the phase modifier sufficient to reduce the solubility of the free acid form, said amount being admixed at a rate sufficient to maintain the temperature of the admixture in a range of about 0° C. to about 5° C.

18. The method according to claim 7 wherein the extraction step is carried out in multiple stages using a cross-current or a countercurrent flow arrangement.

* * * * *